(12) United States Patent
Leuthold

(10) Patent No.: US 8,421,046 B2
(45) Date of Patent: Apr. 16, 2013

(54) OPTICAL SENSOR FOR DETECTING VALUABLE DOCUMENTS AND METHOD FOR KEEPING A SENSOR WINDOW OF THE SENSOR CLEAN

(75) Inventor: Karl-Heinz Leuthold, München (DE)

(73) Assignee: Giesecke & Devrient GmbH, Munich (DE)

( * ) Notice: Subject to any disclaimer, the term of this patent is extended or adjusted under 35 U.S.C. 154(b) by 473 days.

(21) Appl. No.: 12/672,159

(22) PCT Filed: Aug. 8, 2008

(86) PCT No.: PCT/EP2008/006574
§ 371 (c)(1),
(2), (4) Date: Feb. 4, 2010

(87) PCT Pub. No.: WO2009/021697
PCT Pub. Date: Feb. 19, 2009

(65) Prior Publication Data
US 2011/0180694 A1 Jul. 28, 2011

(30) Foreign Application Priority Data
Aug. 10, 2007 (DE) .......................... 10 2007 037 923

(51) Int. Cl.
*G01N 21/15* (2006.01)
*G07D 7/12* (2006.01)

(52) U.S. Cl.
USPC ........... 250/556; 359/509; 356/429; 194/207; 134/37

(58) Field of Classification Search .................. 250/216, 250/555, 556; 194/207; 134/37; 356/429; 359/509
See application file for complete search history.

(56) References Cited

U.S. PATENT DOCUMENTS

| | | | |
|---|---|---|---|
| 3,628,028 A * | 12/1971 | Thorsheim | .................... 250/576 |
| 3,662,174 A | 5/1972 | McMullen et al. | |
| 4,240,691 A * | 12/1980 | Holmqvist et al. | ........... 359/509 |
| 4,266,142 A | 5/1981 | Crawford | |
| 4,767,935 A | 8/1988 | Anderson et al. | |
| 4,786,817 A | 11/1988 | Boissevain et al. | |
| 5,457,539 A | 10/1995 | Sturm | |
| 5,687,964 A * | 11/1997 | Stephan et al. | ................ 271/195 |
| 6,091,501 A * | 7/2000 | Saikanmaki et al. | ......... 356/402 |

(Continued)

FOREIGN PATENT DOCUMENTS

| | | |
|---|---|---|
| DE | 29 12 419 A1 | 12/1979 |
| DE | 4421050 A1 | 12/1994 |

(Continued)

OTHER PUBLICATIONS

International Search Report in PCT/EP2008/006574, Jan. 7, 2009.

(Continued)

*Primary Examiner* — John Lee
(74) *Attorney, Agent, or Firm* — Bacon & Thomas, PLLC

(57) ABSTRACT

In a method for keeping clean a sensor window of an optical sensor for detecting value documents and/or at least one property of value documents which is disposed with at least one portion in a beam path of the sensor, a gas film attached to a surface of the portion is generated on the portion of the sensor window from gas moving relative to the portion.

14 Claims, 3 Drawing Sheets

U.S. PATENT DOCUMENTS

| | | | |
|---|---|---|---|
| 6,305,772 B1 * | 10/2001 | Berkoben et al. | 347/4 |
| 6,543,662 B1 * | 4/2003 | Kuhlmann et al. | 226/97.3 |
| 6,571,620 B2 * | 6/2003 | Moisio | 73/159 |
| 6,890,080 B2 * | 5/2005 | Kalley et al. | 359/509 |
| 7,552,503 B2 * | 6/2009 | Wakao et al. | 15/302 |
| 7,574,033 B2 | 8/2009 | Ishida et al. | |
| 7,913,832 B2 * | 3/2011 | Voser | 194/207 |
| 2003/0142403 A1 * | 7/2003 | Kalley et al. | 359/509 |
| 2003/0197909 A1 * | 10/2003 | Beyer et al. | 359/196 |
| 2006/0233432 A1 | 10/2006 | Ishida et al. | |
| 2007/0278065 A1 * | 12/2007 | Voser | 194/317 |
| 2008/0136091 A1 * | 6/2008 | Shakespeare | 271/227 |
| 2011/0180694 A1 * | 7/2011 | Leuthold | 250/216 |

FOREIGN PATENT DOCUMENTS

| | | |
|---|---|---|
| DE | 37 50 242 T2 | 2/1995 |
| DE | 10225151 A1 | 12/2003 |
| DE | 102004033096 A1 | 2/2006 |
| DE | 11 2004 000 570 T5 | 4/2006 |
| DE | 10 2004 055 761 A1 | 5/2006 |
| EP | 0 537 431 A1 | 4/1993 |
| EP | 0 974 828 A1 | 1/2000 |
| EP | 1 621 883 A2 | 2/2006 |
| GB | 2 147 413 A | 5/1985 |
| GB | 2 379 976 A | 3/2003 |
| JP | 2002-49952 A | 2/2002 |

OTHER PUBLICATIONS

German Search Report for German Patent Publication 10 2007 037 923.6, dated Oct. 12, 2007 (4 pages).

* cited by examiner

OPTICAL SENSOR FOR DETECTING VALUABLE DOCUMENTS AND METHOD FOR KEEPING A SENSOR WINDOW OF THE SENSOR CLEAN

FIELD OF INVENTION

The present invention relates to an optical sensor for detecting value documents and/or at least one optical property of value documents which has a sensor window, and to a method for keeping clean the sensor window of the sensor.

BACKGROUND

Value documents are understood here to be sheet-shaped objects that are to represent for example a monetary value or an authorization and are hence not to be producible at will by unauthorized persons. Hence, they have features that are not easily produced, in particular copied, whose presence is an indication of authenticity, i.e. production by an authorized body. Important examples of such value documents are chip cards, coupons, vouchers, checks and in particular bank notes.

Such value documents, in particular for example bank notes, are often processed by machine. Firstly, upon the transport of such value documents along a transport path of a value-document processing apparatus it is often necessary to check whether, or when, a value document passes a predetermined place. For such a check or detection of a value document there can be employed for example optical sensors in the form of light barriers which have a radiation source for optical radiation of at least one predetermined wavelength as a transmitter and a photodetector for radiation of the predetermined wavelength as a receiver. To avoid soiling of these components for example by dust, or damage by value documents being transported past, there is often located between said components and the transport path a sensor window which is transparent to the employed optical radiation. However, during operation of the apparatus said sensor window also becomes soiled after a certain operation period and must then be cleaned to guarantee trouble-free operation.

Corresponding problems occur with optical sensors serving to detect at least one optical property of value documents, in particular to recognize the type of value documents, for example the denomination of bank notes, or the authenticity of value documents. These also have, for example between the transport path and a detector, at least one sensor window transparent to the employed optical radiation which protects at least part of the sensor, for example the detector, but can itself become soiled and then impair the functioning of the sensor.

For keeping clean the sensor windows they can be periodically cleaned, but this can be elaborate.

SUMMARY

Hence, the present invention is based on the object of providing an optical sensor for detecting value documents and/or at least one optical property of value documents which makes it possible to keep clean a sensor window of the sensor simply and effectively, and of stating a corresponding method for keeping clean the sensor window of the sensor.

This object is achieved by a method for keeping clean a sensor window of an optical sensor for detecting value documents and/or at least one optical property of value documents which is disposed with at least one portion in a beam path of the sensor wherein on the portion of the sensor window a gas film attached to a surface of the portion is generated from gas moving relative to the portion.

The detection of a value document is understood here to mean in particular that it is checked whether a value document is located in a predetermined spatial area, the detection area, and/or whether it is passing a predetermined spatial area, i.e. the detection area. Depending on the result of the check the sensor can then emit a signal indicating the result of the check.

The detection of an optical property of a value document is understood to mean in particular that the sensor emits, upon or after detection of at least a partial area of a value document, a signal representing an optical property of at least the partial area of the value document. During detection, the value document is located in the detection area of the sensor, whereby it can optionally be moving. The optical property can be for example the remissivity and/or transmissivity at a predetermined wavelength of the optical radiation employed by the sensor. However, the optical property can also be the ability to emit luminescence radiation in a predetermined wave range, excited by radiation of at least one predetermined wavelength.

The optical sensor employs optical radiation, i.e. electromagnetic radiation in the ultraviolet and/or visible and/or infrared spectral range, in at least one predetermined wavelength range for detection. Depending on the type of sensor, the optical radiation can be optical radiation for irradiating the value document and/or emanating from the value document.

For separating at least one optical or optoelectronic element of the sensor, for example a detection device for at least part of the employed radiation and/or, if present, a source for at least part of the employed radiation, from the detection area in which the value document is located during detection, the sensor has the sensor window. This is, in the portion upon which at least part of the employed radiation impinges, at least translucent, preferably transparent, to at least part of the radiation employed by the sensor. Said separation permits protection of the corresponding optical or optoelectronic elements from mechanical damage, for example by a value document, and/or soiling from the detection area, for example of a portion of a transport path for transporting value documents past the sensor or through the sensor.

For keeping clean the portion of the sensor window, the gas film is formed. Gas is also understood within the scope of the present invention to be a gas mixture, in particular air.

The sensor window is not blown on with gas in any way here, but rather the gas is guided onto the portion of the sensor window so as to form a gas film attached to the portion. Hence, there is located above the portion a layer of moving gas which impairs, preferably prevents, an impingement of contaminants or dirt particles upon the portion of the sensor window. This can be effected for example by such contaminants or particles being transported away from the portion of the sensor window by the gas film before they can pass to the surface of the portion and accumulate thereon.

The gas film preferably covers the portion of the sensor window all over, the portion preferably having a surface area greater than 100 mm$^2$.

The gas film can in particular be so generated that the Coanda effect occurs. Gas is thereby blown onto a surface so as to form a gas film attached to the surface and optionally following it along a curvature of the surface.

This use of a gas film has the further advantage that it can preferably be so configured that value documents transported past the portion of the sensor window at a small distance can be drawn by the gas film in the direction of the sensor window but without touching it. In this manner it is possible, depending on the configuration of a transport device for transporting the value documents, to do without guidance devices, for example transport belts, directly before the portion of the sensor window. This then permits a detection of a value document across its total width perpendicular to the transport direction.

For forming the gas film there are at least two possibilities, which can be employed alternatively or cumulatively.

According to the first possibility, in the method, the gas for forming the gas film is blown out of at least one blowing nozzle in a component adjacent to the sensor window. The object is then also achieved by a sensor for detecting value documents and/or at least one property of value documents in a detection area by means of optical radiation of at least one wavelength having a source for optical radiation and/or a detection device for optical radiation and at least one sensor window disposed in a beam path between the source or the detection device and the detection area, and at least one component having at least one blowing nozzle through which gas can be so blown out that on at least one portion of the sensor window a gas film attached to a surface of the portion is generated from gas moving relative to the portion. The blowing nozzle can in the simplest case be a portion of a channel, for example a mechanically or laser produced bore, in the component. This possibility offers the advantage that the blowing nozzle can be produced independently of the sensor window by methods coordinated only with the material of the component. Furthermore, a complete separation of sensor window and component is possible, so that the gas does not need to be guided through a portion of an internal space of the sensor.

Preferably, the component in which the at least one blowing nozzle is configured can also serve as a fastening element and/or sealing element for the sensor window and/or the total sensor. This double function permits a simple structure to be achieved.

Additionally or alternatively, the component can also serve as a mechanical guiding element for guiding the value document before the latter is separated from the sensor window portion by the gas film. In this case, too, the double function of the component permits a simplified structure of the sensor in connection with a transport system that transports the value documents to the sensor.

According to the second possibility, in the method, the gas for forming the gas film can be blown out of at least one blowing nozzle in the sensor window. Hence, the object is also achieved by a sensor for detecting value documents and/or at least one property of value documents in a detection area by means of optical radiation of at least one wavelength having a source for the optical radiation and/or a detection device for the optical radiation and at least one sensor window disposed in an optical path between the source or the detection device and the detection area, said sensor window having at least one blowing nozzle through which gas can be so blown out that on at least one portion of the sensor window a gas film attached to a surface of the portion is generated from gas moving relative to the portion.

The following developments and embodiments relate to both above-described possibilities, unless expressly stated otherwise.

In principle the blowing nozzle can be configured at will, provided it is suitable for forming the gas film. In the sensor, the ratio of the length of the portion of the sensor window in the flow direction of the gas in the gas film (on the portion) to the extension of the blowing nozzle in the flow direction of the gas on the portion and in a plane parallel to the gas film on the portion can preferably be greater than 50. If the blowing nozzle has a circular cross section, its extension in the flow direction of the gas on the portion and in a plane parallel to the gas film on the portion can correspond approximately to its diameter, depending on the inclination of the blowing nozzle. Because the gas film is attached to the surface of the sensor window portion, a length or extension in a plane parallel to the gas film can be replaced at least in very good approximation by the corresponding length or extension parallel to the sensor window. This embodiment permits an especially good formation of the gas film at small blowing nozzle diameters and thus low gas consumption.

To achieve a gas film attached to the portion of the sensor window especially uniformly, in the method, the gas is preferably blown out at an angle in the range between 5° and 45°, preferably 15° and 35°, to a plane parallel to the portion of the sensor window. In the sensor, for this purpose, an angle between a blow-out direction in which gas exits from the blowing nozzle and a plane parallel to the portion of the sensor window is in the range between 5° and 45°, preferably 15° and 35°.

Also, it has been found that an especially uniformly attached gas film is attained at low gas consumption when, in the method, in a preferred embodiment, the width of a stream formed by the blown out gas immediately at an opening of the blowing nozzle parallel to the flow direction on the portion and in a plane parallel to the flow direction of the gas in the gas film on the portion is in the range between 0.1 mm and 0.2 mm. In the sensor, for this purpose, the extension of the blowing nozzle in the flow direction of the gas in the gas film above the portion and in a plane parallel to the flow direction of the gas in the gas film on the portion can preferably be in the range between 0.1 mm and 0.2 mm.

Preferably, in the sensor, the blowing nozzle has a circular cross section at least in the area of its mouth. This design permits not only an especially simple production, but also allows a good formation of the gas film.

In many applications, the portion of the sensor window can have approximately the form of a rectangle whose sides are longer than only one to two millimeters. In particular in these cases it is preferable, in the method, that the gas film is formed by blowing out the gas through a plurality of blowing nozzles. The sensor has, for this purpose, at least one further blowing nozzle through which gas for forming the gas film can be blown out. The blowing nozzles can for this purpose be in particular so configured and disposed that the gas streams exiting from the individual blowing nozzles together form the gas film.

The blowing nozzles are preferably configured in the same component or sensor window. Further, they are preferably configured identically.

The blowing nozzles can be disposed in principle at will, provided the gas streams exiting therefrom together form the gas film. An especially uniform, wide film can be formed when, in the sensor, in a preferred embodiment, the blowing nozzles are disposed in a direction perpendicular to a transport direction of the value documents relative to the sensor. In particular, the blowing nozzles can be so aligned that the flow direction of the gas in the gas film extends at least approximately parallel to the transport direction, preferably in the transport direction.

Preferably, mutually adjacent blowing nozzles are at a distance in the range of 2 mm to 5 mm.

Instead of employing a plurality of blowing nozzles for example with a circular cross section in the area of the mouth, however, there can also be employed a blowing nozzle with a slot-shaped cross section, the slot preferably extending perpendicular to the flow direction of the gas in the gas film.

The blowing nozzle or blowing nozzles are disposed at a suitable distance from the portion of the sensor window to be kept clean, which can depend inter alia on the flow velocity of the gas in the particular nozzle as well as the form, dimensioning and inclination of the particular nozzle. Preferably, the distance is between 2 mm and 5 mm.

To permit the formation of the gas film and/or the attachment of the gas film to the portion of the sensor window to be improved, it is possible, in the method, to guide gas blown out of the at least one blowing nozzle, or the blowing nozzles if present, onto the portion by means of an arched guiding surface. In the sensor, there can, for this purpose, be disposed between the at least one blowing nozzle or the blowing nozzles and the portion of the sensor window at least one arched guiding surface by means of which the gas film is guided to the at least one portion of the sensor window. This can advantageously result in additional design options for the sensor, in particular also a reduced size.

The blowing nozzle can be supplied in any way with gas for forming the gas film. In particular, the sensor can have a gas feeding device which supplies gas to the at least one blowing nozzle, so that gas is so blown out therethrough that on at least one portion of the sensor window a gas film attached to a surface of the portion is generated from gas moving relative to the portion. The gas feeding device employed may be for example a gas pump or a gas compressor. In some cases it is also possible, however, to employ a gas tank in connection with a valve by means of which a gas stream can be delivered from the gas tank to the blowing nozzle or blowing nozzles.

If the sensor possesses a plurality of blowing nozzles, gas can be supplied thereto individually by corresponding gas feeding devices; but preferably there is provided a common gas feeding device which supplies the blowing nozzles with gas via a suitable supply device, for example an individual supply pipe leading to the blowing nozzle. Alternatively, it can be recommendable that the at least one blowing nozzle opens into a chamber in which the source and/or the detection device and/or another optical element of the sensor is disposed and which is supplied with gas by the gas feeding device.

The invention is suited in particular for sensors for detecting bank notes or properties of bank notes and particularly for use in bank-note processing apparatuses.

BRIEF DESCRIPTION OF THE DRAWINGS

The invention will hereinafter be explained further by way of example with reference to the drawings. There are shown.

DETAILED DESCRIPTION OF VARIOUS EMBODIMENTS OF THE DISCLOSURE

Figure 1:
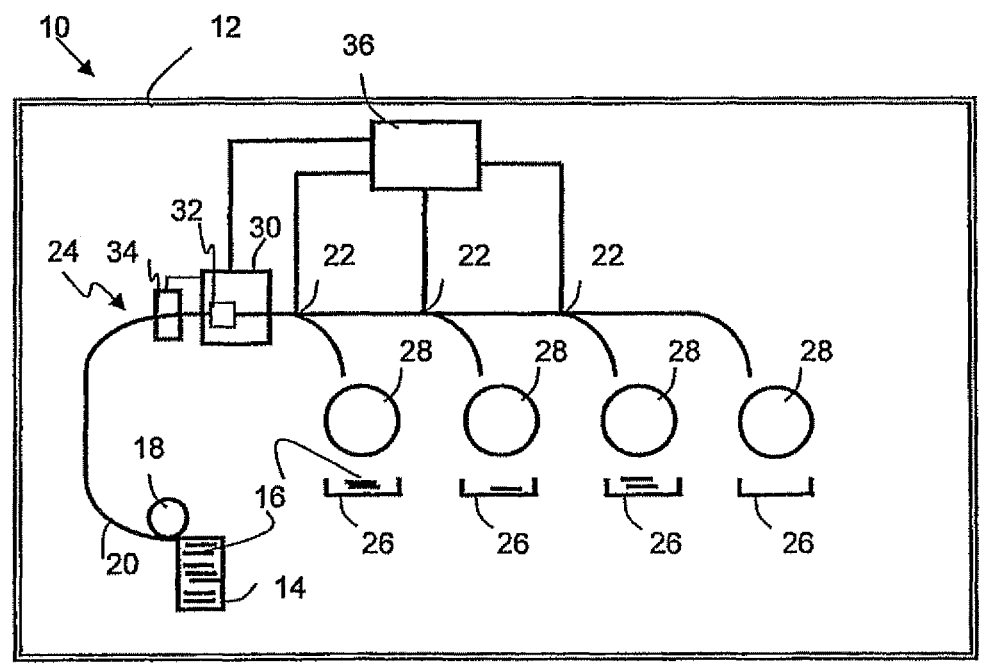
FIG. 1 a schematic view of a bank-note sorting apparatus,
FIG. 2 a schematic lateral sectional view of a sensor according to a first preferred embodiment,
FIG. 3 a schematic plan view of the sensor in FIG. 2,
FIG. 4 a schematic lateral sectional view of a sensor according to a second preferred embodiment,
FIG. 5 a schematic lateral sectional view of a sensor according to a third preferred embodiment, and
FIG. 6 a schematic plan view of the sensor in FIG. 5.

A value-document processing apparatus 10 in FIG. 1, in the example a bank-note processing apparatus, has in a housing 12 an input pocket 14 for inputting value documents 16 to be processed, in the example bank notes, a singler 18 which can access value documents 16 in the input pocket 14, a transport device 20 with gates 22 and, in branches of a transport path 24 given by the transport device 20, after the gates 22, in each case output pockets 26 for receiving value documents processed by means of the value-document processing apparatus 10, with stacker wheels 28 disposed therebefore. Further, the bank-note processing apparatus 10 possesses along the transport path 24 given by the transport device 20 a sensor assembly 30 disposed before the gates 22 for detecting properties of bank notes 16 transported along the transport path 24, as well as a control and evaluation device 32 which is connected via signal connections at least to the sensor assembly 30 and the gates 22 and is configured for evaluating sensor signals of the sensor assembly 30 representing at least one property of a value document 16 detected by the sensor assembly 30, and driving at least one of the gates 22 in accordance with the result of the evaluation of the sensor signals.

The sensor assembly 30 comprises in this exemplary embodiment a sensor 34 for detecting optical properties of security features of bank notes, for example predetermined luminescent substances, and/or of an image of the bank notes, for example for checking for tears, and for ascertaining the denomination of the bank notes. The sensor assembly can further comprise for example an ultrasonic sensor (not shown in FIG. 1) for detecting the state of value documents, for example the presence of adhesive tape.

On the transport path 24 before the sensor assembly 30 in the transport direction there is disposed a sensor 36 for detecting value documents in the form of a light barrier, in the example employing a light curtain, which upon detection of a value document emits a signal to the sensor assembly 30 via a connection (not shown), thereby triggering the detection of the properties of the value document by the sensor assembly 30.

The control and evaluation device 32 detects the signals of the sensor assembly 30 and checks in the example which denomination a bank note 16 detected by the sensor assembly 30 has and whether it is in a circulable state, i.e. suitable for further use as a means of payment, according to at least one predetermined criterion in each case, and authentic. In accordance with the result of the check, the bank note 16 drives at least one of the gates 22 such that the bank note is conveyed by the transport device 20 into an output pocket 26 associated with the check result or corresponding to a certain predetermined type of bank notes, and is stored there.

Upon the processing of value documents there arises dirt, for example dust, in the processing apparatus, which can settle on the optical sensor 34 or the light barrier 36 and impair the functioning thereof.

Figure 2:
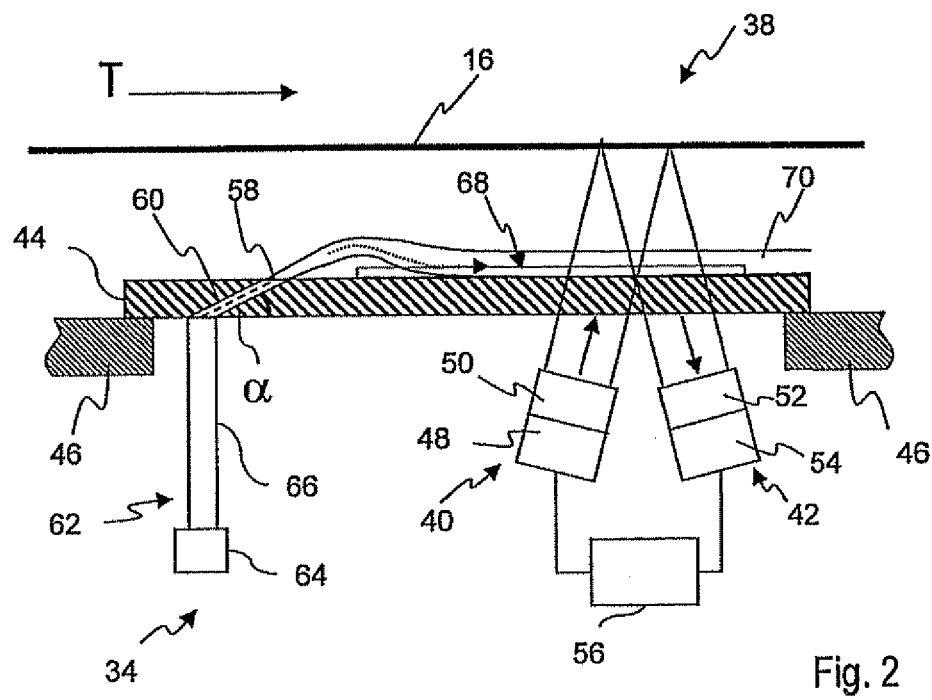
Figure 3:
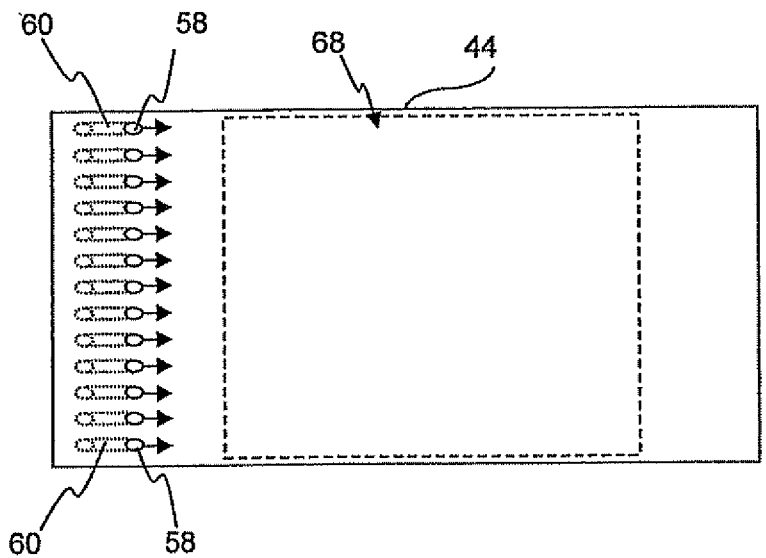

In FIG. 2 the optical sensor 34, which serves to detect luminescence properties of value documents transported past it through its detection area 38 in the transport direction T, is shown schematically in a lateral sectional view, and in FIG. 3 from above.

The sensor 34 has an illumination device 40 for emitting optical excitation radiation, in the example the type of the value documents to be examined has a predetermined wavelength in the range in the infrared spectral range, and a detection device 42 for receiving in spectrally resolved fashion luminescence radiation excited by the excitation radiation in the value document 16 located in the detection area 38 in a predetermined detection wavelength range. The excitation wavelength range and the wavelength range for the luminescence radiation are given by the types of value documents to be examined. Authentic value documents contain at least one substance in which luminescence radiation in the detection wavelength range is excited by the predetermined excitation radiation. The illumination device 40 and the detection device 42 are separated by a sensor window 44 from the detection area 38 and thus the value documents 16 transported therethrough. The sensor window is transparent at least in the wavelength range of the excitation radiation and the detection wavelength range. It is held on a further component, a fastening frame 46, so that the sensor window 44, the fastening frame 46 and a housing bottom portion (not shown in the figures) of the sensor receive the illumination device and the detection device 42 and shield them from dirt, in particular dust, from the surroundings in the value-document processing apparatus 10.

The illumination device 40 has a source 48 for the excitation radiation, for example a gas discharge lamp or a laser diode, and therebehind in the illumination beam path an illumination optic 50, which in the example has a filter passing substantially only the excitation radiation, and an illumination optic which focuses the excitation radiation into the detection area 38 along an illumination area extending perpendicular to the transport direction T across the total maximum width of the types of bank notes intended for checking.

The detection device 42 has, in the example, along a detection beam path starting from the illuminated area of the value document 16 in the detection area 38 a detection optic 52 which images at least part of the area illuminated by the excitation radiation on a value document 16 in the detection area 38 onto a spectrally sensitive detector 54 for spectrally selective detection of the luminescence radiation, and the detector 54. In this example, the detector is a line detector with an upstream narrowband filter which passes substantially only radiation in the predetermined detection wavelength range. The detector possesses for locally resolved detection of the luminescence radiation photodetection elements disposed along a line perpendicular to the transport direction T, which convert luminescence radiation impinging thereupon to electrical detection signals.

For detecting the luminescence properties, the sensor is operated in pulsed fashion, for which purpose it has a control means 56 which drives the illumination device to emit excitation radiation pulses and, temporally coordinated therewith, the detection device 42 to detect detection radiation pulses excited by the excitation radiation pulses. Said control means 56 relays detection signals received from the detection device 42, after further processing, to the control and evaluation device 32.

In the optical paths, formed by the illumination beam path into the detection area 38 as well as the detection beam path, between the radiation source 48 or the detection device 42 and the detection area 38 or the value document 16 there is disposed the sensor window 44 in which there are configured upstream of the detection area 38, regarded in the transport direction T, along a line extending perpendicular to the transport direction T, blowing nozzles 58—identically configured in this example—which are formed by the mouths of blowing channels 60 extending linearly through the sensor window 44.

The blowing channels 60 and thus the blowing nozzles 58 are inclined at an angle $\alpha$ relative to the plane of the sensor window. The gas feeding device 62 and the blowing nozzles 58 are configured to be so coordinated with each other that the gas exits from the blowing nozzles 58 at the angle $\alpha$ in the direction of the transport of the value documents 16. The angle is in the range between 5° and 45°, preferably 15° and 35°, in the example 25°.

For feeding the blowing nozzles 58 with a gas, in the example air, there is provided a gas feeding device 62 which comprises a pump 64 and a supply pipe 66 connecting said pump to the blowing channels 60 and thus the blowing nozzles 58.

The diameter of the blowing channels 60 and thus also of the blowing nozzles 58 and of the respective gas stream exiting therefrom immediately at the blowing nozzle can in general be preferably between 0.1 and 0.2 mm. In the example it is chosen to be about 0.15 mm.

The distance between adjacent blowing nozzles 58, i.e. the length of the shortest connection line between the edges of two adjacent blowing nozzles, can be between 2 mm and 5 mm; in the example it is chosen to be 3 mm.

The configuration of the individual blowing nozzles 58, the distance between the blowing nozzles 58 and the strength of the gas stream are so chosen that a planar gas film 70 attached to a surface of a portion 68, located in the detection area, of the sensor window 44 is generated from gas moving relative to the portion 68. The configuration and arrangement of the blowing nozzles 58 as well as the strength of the gas stream are preferably so chosen that the gas film 70 is attached to the portion 68 as a result of the Coanda effect. In the example, the portion 68 is longer in the transport direction than 1 cm and thus more than ten times longer than the extension of the blowing nozzles 58 in the plane of the sensor window 68 and thus a transport plane extending parallel thereto.

Although pulsed operation is conceivable, the gas film 70 is preferably formed continuously at least while an individual value document 16 is being transported past, preferably while the stream is being processed in the case of processing of a stream of singled value documents generated for example from a stack.

In this manner, dirt moving in the direction of the sensor window 44 cannot pass onto the portion 68 of the sensor window 44, but is rather kept off the sensor window 44 and guided away by the gas film 70. At the same time, there can result a force directed in the direction of the sensor window 44 on a value document 16 transported past.

In a variant of this exemplary embodiment, the detection device 42 can also be given by a spectrometer.

Figure 4:
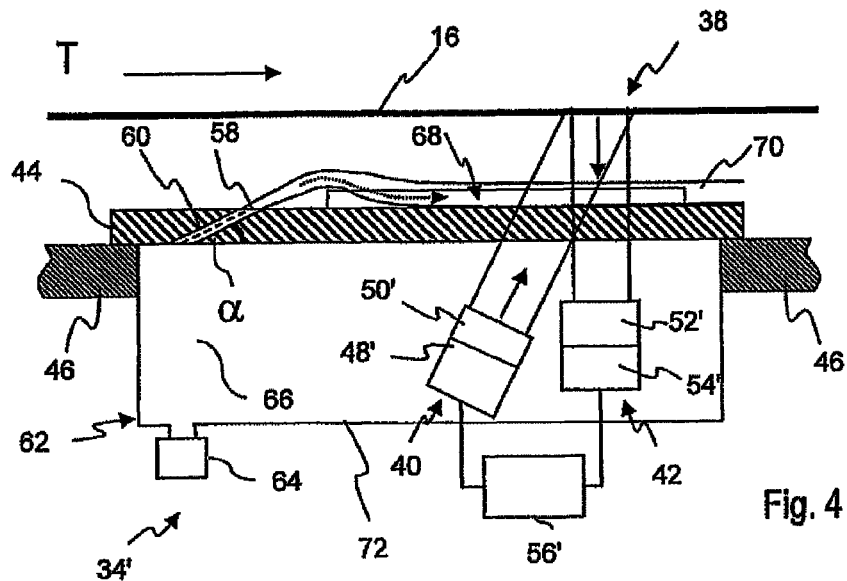

A second exemplary embodiment illustrated in FIG. 4 differs from the first exemplary embodiment only by the gas supply to the blowing channels 60 and by the sensor 34'. Hence, the same reference signs are employed for unchanged parts as in the first exemplary embodiment and the explanations thereof also apply here accordingly.

The optical sensor 34' now serves to detect an image of a value document 16 transported past it, in the visible part of the optical spectrum, and possesses, like the sensor 34, an illumination device 40' and a detection device 42'.

The illumination device 40' has a source 48' for white light and, in the optical path into the detection area, an illumination optic 50' which generates with the light of the source 48' in the detection area 38 a strip-shaped illumination area extending perpendicular to the transport direction.

The detection device 42' possesses along an optical path starting from the detection area 38 a detection optic 52' and a line camera 54' working in the visible range of the optical spectrum, whose detection elements are disposed in a line perpendicular to the transport direction T. The detection optic 46' images a part, located in the detection area 38 in the illumination area, of a value document 16 onto the line camera 54'.

The illumination device 40' and the detection device 42' are again connected to a control means 56' which, like the control means 56, drives the illumination device and the detection device in accordance with the transport speed in the known way such that an image of the value document is generated line by line.

Unlike the sensor of the first exemplary embodiment, the illumination device 40' and detection device 42' are disposed in a gastight chamber 72 closed by the sensor window 44, into which the blowing channels 60 open, on the one hand, and which is connected to the pump 64, on the other hand. The pump 64 and the chamber 72 thus form a gas supplying device by means of which gas can be so supplied to the blowing nozzles that the gas is so blown out therethrough that on the portion 68 of the sensor window 44 a gas film 70 attached to the surface of the portion 68 is generated from gas moving relative to the portion 68.

Figure 5:
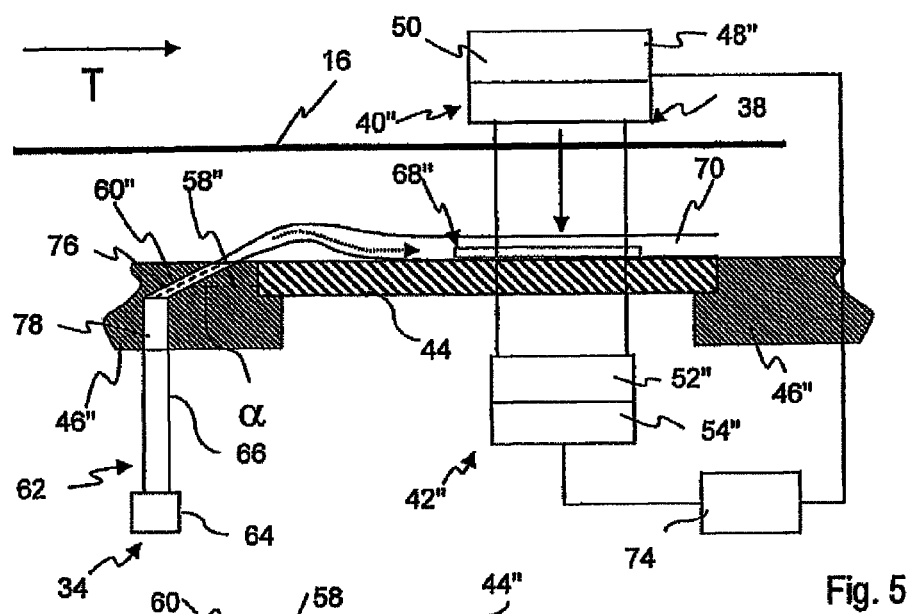
Figure 6:
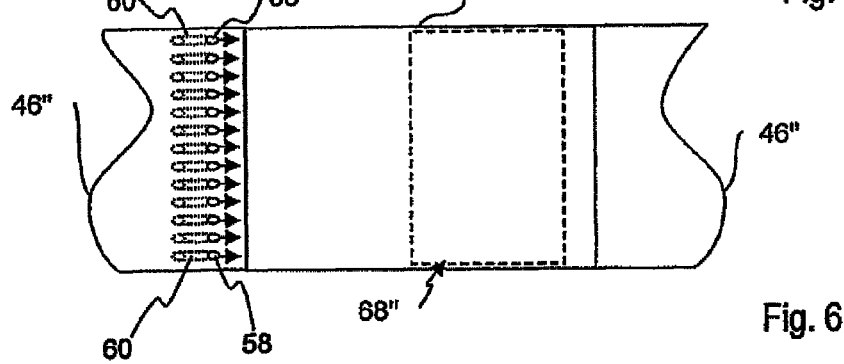

A third exemplary embodiment in FIG. 5 and FIG. 6 differs from the first exemplary embodiment firstly in that the light barrier 36 is now constructed analogously to the sensor of the first exemplary embodiment, and secondly in that the blowing nozzles are now configured not in the otherwise unchanged sensor window but in another component of the sensor. Hence, the same reference signs are employed for corresponding parts as in the first exemplary embodiment and the explanations thereof also apply accordingly to this exemplary embodiment.

The sensor 34" serves only to detect a value document transported past in the manner of a transmitted light barrier with a light curtain. The sensor 34" has an illumination device 40" serving as a transmitter and, serving as a receiver, a detection device 42" for radiation of the illumination device 40" which detects radiation emitted thereby along an optical path through a transport plane along which the value documents are transported. The detection area 38 thus lies between the two devices. An evaluation device 74 drives the illumination device 40" to emit optical radiation and receives detection signals of the detection device 42" and evaluates them partly. In accordance with the result of the evaluation, the latter then drives the sensor assembly 30.

The illumination device 40" has sources 48", disposed equidistantly along a line extending perpendicular to the transport direction T, for optical radiation for illuminating the detection area 38, in the example light-emitting diodes, and in the optical path from the sources 48" to the detection device 42" an illumination optic 50" for focusing the radiation emitted by the sources 48".

The detection device 42" accordingly has a detector 54" with photodetection elements disposed along a line extending perpendicular to the transport direction T and each associated with one of the sources 48", and a detection optic 50"" for focusing the radiation of the sources 48" onto the particular photodetection elements.

The evaluation device 74 receives detection signals of the detection device 42", more precisely of the detectors therein, and ascertains whether the optical path from the illumination device 40" to the detection device 42" has been interrupted. In this case it outputs a corresponding signal. In a preferred variant, signals can be output separately for each of the photodetection elements. From the temporal position of the signals it can then be ascertained whether the leading edge of the value document extends orthogonally to the transport direction T or whether the value document is being transported askew.

Between the detection area 38 and the detection device 42" there is disposed the sensor window 44", which does not differ from the sensor window 44 except for configuration of the blowing channels. The portion 68" to be kept clean in the sensor window 44" comprises the area of the sensor window 44" illuminated by the radiation of the illumination device 40".

The sensor window 44" is held in a fastening frame 46" in which there are again configured blowing nozzles 58 which are formed by the mouth portions of blowing channels 60". These have two channel portions of which the channel portion 76 opening on the surface facing the detection area 38 is configured like the blowing channels 60 in the first exemplary embodiment. The second channel portions 78 are bent relative to the direction of the first channel portions and extend substantially orthogonally to the surface of the sensor window 44".

For feeding the blowing channels 60" with gas there is provided a gas feeding device which is configured as in the first exemplary embodiment, so that the same reference signs are employed therefor and the explanations apply here too.

In this manner, gas can be so blown out through the blowing nozzles that on the portion 68" of the sensor window 44" a gas film 70 attached to a surface of the portion 68" is generated from gas moving relative to the portion, which keeps the sensor window clean. This exemplary embodiment offers the advantage that the channels need not necessarily be configured in the sensor window, which is possibly more difficult to machine, but rather the material of the component, i.e. in the example the fastening frame, can be chosen accordingly.

In a variant of the sensor, the sensor can also be configured as a transmission sensor, instead of a light barrier.

Further, the illumination device and thus the sources 58" can also be disposed behind a sensor window, which can be configured like the sensor window 44 or 44". For supplying gas, either the same gas feeding device can be employed, or two separate feeding devices can be provided.

Different aspects of the exemplary embodiments can also be interchanged. Thus, the blowing nozzles can also be configured in the fastening frame in the first two exemplary embodiments.

Also, it is possible to configure an arched guiding surface downstream of the blowing nozzles, which improves the formation of the gas film.

The invention claimed is:

1. A method for keeping clean a sensor window of an optical sensor for detecting value documents and/or at least one property of value documents which is disposed with at least one portion in a beam path of the sensor, comprising the steps:
   generating a moving gas film on the at least one portion of the sensor window so that the gas film is attached to a surface of the at least one portion by the gas moving in a direction relative to the at least one portion; and
   blowing the gas out from at least one blowing nozzle at an angle in the range between 15° and 35° with respect to a plane parallel to the at least one portion of the sensor window,
   wherein a stream of gas formed by the blown out gas from an opening of the at least one blowing nozzle moving parallel to the flow direction on the at least one portion and in a plane parallel to the flow direction of the gas in the gas film on the at least one portion has a width in the range between 0.1 mm and 0.2 mm.

2. The method according to claim 1, wherein the gas is blown out from the at least one blowing nozzle in a component adjacent to the sensor window.

3. The method according to claim 1, wherein the gas is blown out from the at least one blowing nozzle in the sensor window.

4. The method according to claim 1, wherein the gas film is formed by blowing out the gas through a plurality of blowing nozzles.

5. The method according to claim 1, wherein the gas blown out from the at least one blowing nozzle is guided onto the at least one portion by an arched guiding surface.

6. A sensor for detecting value documents and/or at least one property of value documents in a detection area using optical radiation of at least one wavelength, comprising:
- a source for optical radiation and/or a detection device for optical radiation;
- at least one sensor window disposed in a beam path between the source or the detection device and the detection area; and
- at least one component having at least one blowing nozzle arranged to blow out a gas stream over at least one portion of the sensor window so that a gas film will be attached to a surface of the portion by the gas moving relative to the portion,
- wherein the at least one blowing nozzle blows out the gas stream at an angle in the range between 15° and 35°, wherein said angle is between a blow-out direction in which gas exits from the blowing nozzle and a plane parallel to the portion of the sensor window, and
- wherein the blowing nozzle is configured to form a stream of gas from an opening of the at least one blowing nozzle having a width in the range between 0.1 mm and 0.2 mm, said stream of gas being in the flow direction of the gas in the gas film above the at least one portion and in a plane parallel to the flow direction of the gas in the gas film on the at least one portion.

7. A sensor for detecting value documents and/or at least one property of value documents in a detection area using optical radiation of at least one wavelength, comprising:
- a source for the optical radiation and/or a detection device for the optical radiation; and
- at least one sensor window disposed in an optical path between the source or the detection device and the detection area, said at least one sensor window having at least one blowing nozzle arranged to blow out a gas stream over at least one portion of the sensor window so that a gas film will become attached to a surface of the portion from gas moving relative to the portion,
- wherein the at least one blowing nozzle blows out the gas stream at an angle in the range between 15° and 35°, wherein said angle is between a blow-out direction in which gas exits from the blowing nozzle and a plane parallel to the portion of the sensor window, and
- wherein a portion of the blowing nozzle is configured to form a stream of gas having a width in the range between 0.1 mm and 0.2 mm, said stream of gas being in the flow direction of the gas in the gas film above the at least one portion and in a plane parallel to the flow direction of the gas in the gas film on the at least one portion.

8. The sensor according to claim 6, wherein the ratio of the length of the portion of the sensor window in the flow direction of the gas in the gas film to the width of the stream of gas from the blowing nozzle in the flow direction of the gas on the at least one portion and in a plane parallel to the gas film on the portion is greater than 50.

9. The sensor according to claim 6, wherein the blowing nozzle includes a mouth and has a circular cross section at least in the area of the mouth.

10. The sensor according to claim 6, wherein at least one further blowing nozzle is provided that is arranged to blow out additional gas for forming the gas film.

11. The sensor according to claim 10, wherein the blowing nozzles are disposed in a direction perpendicular to a transport direction of value documents relative to the sensor.

12. The sensor according to claim 6, wherein between the at least one blowing nozzle and the portion of the sensor window there is disposed at least one arched guiding surface arranged to guide the gas film to the at least one portion of the sensor window.

13. The sensor according to claim 6, including a gas feeding device which supplies gas to the at least one blowing nozzle.

14. The sensor according to claim 13, wherein the at least one blowing nozzle opens into a chamber in which the source and/or the detection device and/or another optical element of the sensor is disposed, and into which gas is supplied by the gas feeding device.

* * * * *